United States Patent
Wang et al.

(10) Patent No.: US 10,206,972 B2
(45) Date of Patent: Feb. 19, 2019

(54) ANTI-VASCULAR DISEASE AND ANTITUMOR PHARMACEUTICAL COMPOSITION AND USE THEREOF

(71) Applicants: Guangzhou Yidai Pharmaceutical Co., Ltd., Gaungzhou (CN); Sun Yat-sen University, Guangzhou (CN)

(72) Inventors: Hua Wang, Guangzhou (CN); Huanchun Liang, Guangzhou (CN)

(73) Assignees: GUANGZHOU YIDAI PHARMACEUTICAL CO., LTD. (CN); SUN YAT-SEN UNIVERSITY (CN)

(*) Notice: Subject to any disclaimer, the term of this patent is extended or adjusted under 35 U.S.C. 154(b) by 0 days.

(21) Appl. No.: 15/301,092

(22) PCT Filed: Dec. 30, 2014

(86) PCT No.: PCT/CN2014/095540
§ 371 (c)(1),
(2) Date: Dec. 15, 2016

(87) PCT Pub. No.: WO2015/149559
PCT Pub. Date: Oct. 8, 2015

(65) Prior Publication Data
US 2017/0087208 A1    Mar. 30, 2017

(30) Foreign Application Priority Data
Apr. 3, 2014   (CN) .......................... 2014 1 0133926

(51) Int. Cl.
| A61K 38/14 | (2006.01) |
| A61K 31/137 | (2006.01) |
| A61K 31/573 | (2006.01) |
| A61K 31/661 | (2006.01) |
| A61K 9/00 | (2006.01) |
| A61K 9/16 | (2006.01) |
| A61K 9/19 | (2006.01) |
| A61K 9/50 | (2006.01) |
| A61K 31/167 | (2006.01) |
| A61K 9/51 | (2006.01) |

(52) U.S. Cl.
CPC ............ *A61K 38/14* (2013.01); *A61K 9/0019* (2013.01); *A61K 9/1658* (2013.01); *A61K 9/19* (2013.01); *A61K 9/5094* (2013.01); *A61K 9/5153* (2013.01); *A61K 9/5161* (2013.01); *A61K 31/137* (2013.01); *A61K 31/167* (2013.01); *A61K 31/573* (2013.01); *A61K 31/661* (2013.01); *A61K 9/5115* (2013.01); *A61K 9/5192* (2013.01)

(58) Field of Classification Search
CPC ..... A61K 38/14; A61K 31/137; A61K 31/573
See application file for complete search history.

(56) References Cited

U.S. PATENT DOCUMENTS

2009/0105329 A1* 4/2009 Chiao .................. A61K 31/167
514/449

FOREIGN PATENT DOCUMENTS

| CN | 1391901 A | | 1/2003 |
| CN | 101284127 A | * | 10/2008 |
| CN | 102225054 A | | 10/2011 |
| CN | 102294035 A | | 12/2011 |
| CN | 104027808 A | | 9/2014 |

OTHER PUBLICATIONS

CN 101284127 ("the '127 publication"; English machine translation.*
International Search Report PCT/CN2014/095540; International Filing Date: Dec. 30, 2014; 2 Pgs.

* cited by examiner

*Primary Examiner* — H. Sarah Park
(74) *Attorney, Agent, or Firm* — Schmeiser, Olsen & Watts, LLP

(57) ABSTRACT

An anti-vascular diseases and antitumor pharmaceutical composition is provided in the present invention, and it includes effective ingredients including bleomycin antitumor antibiotic, adrenal glucocorticoid, epinephrine or pharmaceutically acceptable salts thereof in a weight ratio of (1-8):(2-5):(0.00005-0.001). The pharmaceutical composition provided can be used for treatment of vascular diseases and tumors.

12 Claims, 1 Drawing Sheet

Fig. 1
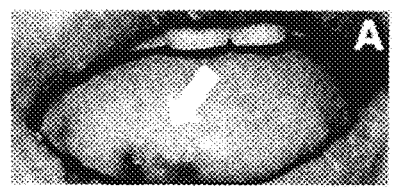 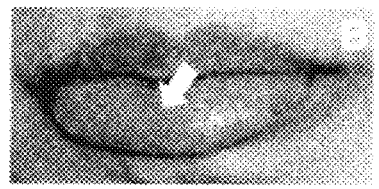
Fig. 2A  Fig. 2B
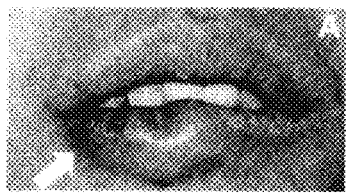 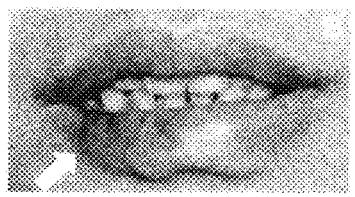
Fig. 3A  Fig. 3B
 
Fig. 4A  Fig. 4B
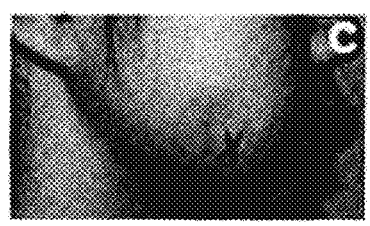 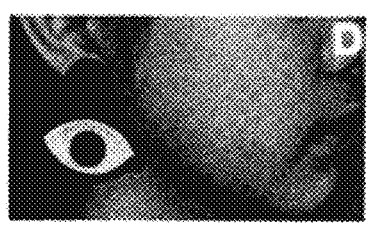
Fig. 4C  Fig. 4D

ANTI-VASCULAR DISEASE AND ANTITUMOR PHARMACEUTICAL COMPOSITION AND USE THEREOF

CROSS-REFERENCE TO RELATED APPLICATIONS

This application claims priority to PCT Application No. PCT/CN2014/095540, having a filing date of Dec. 30, 2014, based off of Chinese application No. 201410133926.8 having a filing date of Apr. 3, 2014, the entire contents of which are hereby incorporated by reference.

FIELD OF TECHNOLOGY

The following belongs to the field of pharmaceutical formulations, and it particularly refers to an anti-vascular disease and antitumor pharmaceutical composition.

BACKGROUND

Vascular disease includes vascular malformations and vascular tumors. The vascular malformations can be blood vessel malformations, lymphatic malformations, or mixed lymphatic-blood vessel malformations; the blood vessel malformations can be blood capillary malformations, venous malformations or arteriovenous malformation, and the like; the vascular tumors include benign hemangioma commonly found in infants, traumatic hemangioma, blood capillary tumors and malignant hemangiosarcoma. With regarding to the vascular disease, clinically traditional therapeutic method includes surgical treatment, sclerotherapy, endovascular embolization treatment, microwave-thermocoagulation surgical treatment, and laser therapy, etc. However, these traditional therapeutic methods will cause large surgical wounds, high risk of bleeding and low cure rate for large vascular diseases.

Tumor is one of the most severe diseases to threaten the human health and life. In the latter half of $20^{th}$ century, the morbidity and mortality of tumors in the world are increasing. Especially after 1970s, the morbidity of tumors is increasing by 3%-5% every year. Nowadays, there are nearly 7 million people that have died from cancer every year in the world, wherein 24% of them happened to live in China. In China, the surviving patients and cured patients are only 13% in the total cancer patients, meanwhile, there are 2.6 million new patients suffering every year. At present, surgical treatment, chemotherapy and radiation therapy are three therapeutic methods commonly used when human beings fight cancer. However, none of them can totally eliminate all the cancer cells in the body, the risks of relapse and matastasis still exist. Besides, the chemotherapy and radiation therapy have severe toxic-side effects.

Recently, it has been reported that a "three-combined medication" combined of pingyangmycin, dexamethasone and lidocaineis used to treat vascular diseases through tumor-intracavity injection in a large amount of literatures in China. A "three-combined medication", combined of pingyangmycin, dexamethasone and lidocaine, disclosed in Chinese patent application CN01115049.1, entitled "an injection for treatment of hemangioma", has two disadvantages that 1) when the "three-combined medication" combined of pingyangmycin, dexamethasone and lidocaineis used in tumor-intracavitary injection for large vascular malformations, especially for arteriovenous malformation, the residence time of this medication staying in the tumor intracavity is too short to obtain and maintain an effective medication concentration, which leads to an unsatisfied therapeutic effect; meanwhile a usage of pingyangmycin in a large dose in the short term may initiate toxic-side effects, such as gastrointestinal tract response, alopecia, bone marrow hemopoietic function suppression and pulmonary fibrosis, etc.; 2) as the lidocaine and pingyangmycin are both the allergens of anaphylactic shock, their combination increases the risk of allergic reaction and complicates the antianaphylactic treatment, and clinically the injection of pingyangmycin "three-combined medication" was reported to initiate the anaphylactic shock and threaten patients' lives.

Pingyangmycin is a bleomycin antitumor antibiotic, and is one of the preferred medications for treating the squamous-cell carcinoma. Tumor-intracavity injection and arterial perfusion can be used to increase the medication concentration in the tumor area and decrease the systemic side-effect. However, the therapeutic effect is still unsatisfied even applying the tumor-intracavity injection and arterial perfusion, due to the rich vascular circulation in the tumor area. In addition, hematopoiesis and immunologic functions suppression may often occurs during the treatment, so as to initiate severe complications, because of the insufficient targeting for tumors. A formulation carrying antitumor drug particles has been disclosed in Chinese patent application CN201110165034.2, wherein the antitumor drug particles are guided into the multidrug resistant mesenchymal stem cells which are taken as the drug particles carriers for the targeted therapy of tumors, whereby the toxic-side effect is reduced. A dual targeting anti-malignant tumor magnetic nanoparticles drug carrier system is provided in Chinese patent application CN201110248233.X, wherein the ligands and antitumor drugs are combined and secured on the surface of magnetic nanoparticles, and the targeting chemotherapy is achieved through external magnetic force and specific binding between ligands and tumor cells. However, the ligands have a large molecular weight and a weak penetration ability, which injures the therapeutic effect.

It has shown advantageous therapeutic effect for the clinical research of treatment of oral and maxillofacial blood vessel tumors by combining pingyangmycin with dexamethasone, but with regarding to arteriovenous malformation with fast blood velocity, the therapeutic effect is poor, and clinical reports about severe allergic reactions even the anaphylactic shock still exist.

SUMMARY

An aspect relates to a new pharmaceutical composition, which can be used for the treatment of vascular diseases and tumors, with a feature of small risk of anaphylactic shock, and it is helpful to improve the therapeutic effect.

In order to achieve this aspect, embodiments of the invention provide the following technical solution:

an improved anti-vascular diseases and antitumor pharmaceutical composition comprises effective ingredients comprising bleomycin antitumor antibiotic, adrenal glucocorticoid, epinephrine or pharmaceutically acceptable salts thereof in a weight ratio of (1-8): (2-5): (0.00005-0.001). The effective ingredients of the pharmaceutical composition may only consist of above three substances.

Preferably, the weight ratio of bleomycin antitumor antibiotic, adrenal glucocorticoid and epinephrine is 8:5:0.0001. It is advantageous to exert the pharmacodynamic supplementary and synergistic effect of the three pharmaceutical ingredients to the greatest extent, by choosing such preferable ratio.

The pharmaceutical composition of embodiments of the present invention comprises bleomycin antitumor antibiotic, adrenal glucocorticoid and epinephrine, and their total weight is present in an amount of 20-90 wt. %, based on the pharmaceutical composition. When used for treatment, it can be diluted to the required concentration with normal saline or glucose injection as medically indicated. If the pharmaceutical composition is in a dosage form of injection, the total weight of the bleomycin antitumor antibiotic, adrenal glucocorticoid and epinephrine may account for a lower percent, e.g., about 0.3%, of the injection.

Specifically, the bleomycin antitumor antibiotic can be at least one selected from a group consisting of pingyangmycin, bleomycin, boanmycin and boningmycin, preferably pingyangmycin, and they can be purchased from various drug manufacturers.

Specifically, the adrenal glucocorticoid can be at least one selected from a group consisting of dexamethasone, prednisolone, prednisone, hydrocortisone, cortisone, triamcinolone, betamethasone, beclomethasone, dexamethasone acetate and dexamethasone sodium phosphate, preferably dexamethasone, and they can be purchased from various drug manufacturers. Two kinds of known commercially available dexamethasone are dexamethasone acetate and dexamethasone sodium phosphate.

The pharmaceutical composition of embodiments of the present invention comprises the balance of pharmaceutically acceptable auxiliaries, such as pH regulators, mannitol, magnetic nanomaterials, control-released materials, targeting binding proteins, and the like, except for the above effective ingredients. One skilled in the art could choose specific auxiliary according to the dosage form of the pharmaceutical composition.

Specifically, the pH regulator can be, but not limited to, at least one selected from a group consisting of sodium hydroxide, disodium hydrogen phosphate, sodium dihydrogen phosphate, hydrochloric acid, acetic acid, and sodium acetate.

The pharmaceutical composition of embodiments of the present invention may in a dosage form of injection, freeze-dried powders, or microspheres, wherein the microspheres can be albumin microspheres, magnetic nano-microspheres, control-released magnetic nano-microspheres, cellular targeted magnetic nano-microspheres, etc. The pharmaceutical composition of embodiments of the present invention can be prepared into corresponding dosage form through pharmaceutically common or existing preparation processes.

The pharmaceutical composition of embodiments of the present invention may contain pharmaceutically acceptable auxiliaries, such as magnetic nanomaterials, control-released materials, targeted binding proteins, etc., according to the dosage form to be prepared.

The magnetic nanomaterial can be one or more selected from a group consisting of nano iron, $Fe_3O_4$, $\gamma$-$Fe_3O_4$, other metal ferrites such as MnZn ferrite, and the silica-wrapped magnetic nano-microspheres.

The control-released materials may be one or more selected, but not limited to, from a group consisting of poly lactide-glycolide acid, polyving akohol and gelatin.

The targeted binding proteins may be one or more selected from a group consisting of humanized antibodies, ligands, binding proteins, agglutinins and small molecular compounds, preferably one or more of binding proteins, agglutinins and humanized antibodies. In the present technical field, the targeting varies with the lesions, e.g., von Willebrand factors, VEGFR-1, VEGFR-2 and Tie2, etc., can act as the bio-targets of endothelial cells for vascular disease; CD44, CD133, ALDH1, EGFR, SCCA, etc., can act as the bio-targets of tumor cells; CD34, CD14, CD105 and CD133, etc., can act as the bio-targets of stem cells. With regarding to above bio-targets, one skilled in the art can select the corresponding antibodies.

Binding protein is one type of proteins capable of specifically binding to the bio-targets of cells. For example, protein A (staphylococcal protein A; SPA) and protein G are non-antibody binding proteins, which can bind to most types of Fc segments of IgG, and have been widely used for the indirect sorting of magnetic cells. Recently it has been successively found that other binding proteins (Skerra A, 2007), such as AdNectin specifically binding to VEGF-R2, Avimer specifically binding to IL-6, small molecular compounds Plerixafor specifically binding to CXCR4, and the like, can also act as targeting binding proteins, thus making magnetic particles labeled by bleomycin anti-tumor antibiotic (e.g. pingyangmycin) specifically bind to the targeting cells to exert lethal effects.

Agglutinins existed in the nature, such as the Con A (conconvalina), WGA (wheat germ agglutinin), PNA (peanut agglutinin), SBA (soybean agglutinin), DBA (dolichosbifows agglutinin) or ulex europaeus Ilectin, etc., are proteins capable of binding to saccharides, wherein the DBA mainly bind to the vascular endothelial cells of various tissues, and Ulex europaeus Ilectin can bind to L-fucosyl on the endothelial cell surface.

In an example, the pharmaceutical composition of embodiments of the present invention can be prepared in the dosage form of injection as following process of weighting bleomycin antitumor antibiotic, epinephrine, and adrenal glucocorticoid in a proper proportion; dissolving them completely in their respective solubilizers; mixing them to obtain a mixture solution; adjusting the pH to 4.0-6.5 through pH regulator; whereby the injection is obtained.

In an example, the pharmaceutical composition of embodiments of the present invention can be prepared in the dosage form of freeze-dried powder-injection as following processes of weighting bleomycin antitumor antibiotic and epinephrine in a proper proportion; dissolving them completely in water; mixing them to obtain a mixture solution; adjusting the pH to 4.0-6.5 through pH regulator; freeze drying the solution; whereby the freeze-dried powder-injection containing epinephrine is obtained as bottle A, and the injection containing adrenal glucocorticoid such as dexamethasone is reserved as bottle B.

In an example, the pharmaceutical composition of embodiments of the present invention can be prepared in the dosage form of albumin microspheres as following process of weighting bleomycin antitumor antibiotic and adrenal glucocorticoid in a proper proportion; dissolving them completely in their respective solubilizers and mixing them together; adding epinephrine to obtain a mixture solution; preparing albumin microspheres through the emulsifying-curing method. The emulsifying-curing method can be applied as following detailed process of well mixing the obtained mixture solution with 25 wt. % albumin solution, then adding the mixture into the vegetable oil to emulsify, and then adding them into the soybean oil at a temperature of 140° C. to cure, washing them with petroleum ether and diethyl ether after cooling, finally drying and collecting to obtain the albumin microspheres.

In an example, the pharmaceutical composition of embodiments of the present invention can be prepared in the dosage form of magnetic nano-microspheres as following process of 1) weighting bleomycin antitumor antibiotic and adrenal glucocorticoid in a proper proportion; dissolving them completely in their respective solubilizers and mixing them together; adding epinephrine to obtain a mixture solution;
2) dissolving the sealing agents and magnetic nanomaterials (preferably silica-wrapped magnetic nano-microspheres) into aqueous solution in a proper proportion, stirring and adding them into the mixture solution of step 1), then adding liquid paraffin containing Span85 slowly, placing it in an ice bath after emulsifying, adding formaldehyde and isopropanol successively, and filtrating after stirring, then washing them with anhydrous ether and acetone, finally drying and sieving, thus the magnetic nano-microspheres are prepared.

In an example, the pharmaceutical composition of embodiments of the present invention can be prepared in the dosage form of control-released magnetic nano-microspheres as following process of 1) weighting bleomycin antitumor antibiotic and adrenal glucocorticoid in a proper proportion; dissolving them completely in their respective solubilizers and mixing them together; adding epinephrine to obtain a mixture solution;
2) adding dichloromethane solution in which magnetic nanomaterials and poly lactide-glycolide acid (PLGA) have been dissolved in the pre-emulsifying reactor beforehand, then adding the mixture solution of step 1), stirring at a high speed to obtain a water-in-oil compound pingyangmycin pre-emulsion, which is subsequently added slowly into the PVA aqueous solution and stirred to form a water-in-oil-in-water (W/O/W) multiple emulsion, then slowing down the stirring rate and obtaining the PLGA microspheres after gradual curing, drying the microspheres through the freeze-drying method after washing to obtain the control-released magnetic nano-micropheres.

In an example, the pharmaceutical composition of embodiments of the present invention can be prepared in the dosage form of targeted magnetic nano-microsphere as following process: Firstly, prepare magnetic nano-micropheres or control-released magnetic nano-micropheres by methods mentioned above. Then, mix the binding protein solution with the nano-micropheres before drying, to make the binding protein adhere to the surface of nano-microspheres, and dry them through freeze-drying method after washing to obtain the binding protein targetedmagnetic nano-micropheres.

The pharmaceutical composition of embodiments of the present invention can be applied in therapy through tumor-intracavity injection, arterial injection or intravenous injection. The pharmaceutical composition of embodiments of the present invention may be diluted to a proper dose before treatment. For example, 1) when applying the tumor-intracavity injection, dissolve 4-8 mg pharmaceutical composition of embodiments of the present invention in 2-4 ml normal saline to operate the slow tumor-intracavity injection, for small vascular malformation, such as venous malformations and lymphatic malformations; while dissolve 4-16 mg pharmaceutical composition of embodiments of the present invention in 4-8 ml normal saline to operate the slow tumor-intracavitary injection, for large venous malformations. Repeat the injection after an interval period of 15-30 days, with a treatment course of 5 times and the total dose of no more than 240 mg. Preferably, a tumor intracavitary injection concentration of 1 mg/ml is applied for skin cancer and HNSCC. 2) When applying arterial injection, dissolve 4-8 mg pharmaceutical composition of embodiments of the present invention in 3-25 ml normal saline containing anticoagulants to operate one arterial injection, with a dose of 8 mg for adult each time. The medication is administered once every 2-4 weeks for vascular malformation, with a dose of 16-40 mg for detectable curative effect; while the medication is administered 3-5 times each week for malignant tumors with a dose of 16-80 mg for detectable curative effect. 3) When applying intravenous injection, dissolve 4-16 mg pharmaceutical composition of embodiments of the present invention in 4-20 ml normal saline or glucose to operate a slow intravenous injection. The medication is administered once every 2-4 weeks for vascular malformation, with a dose of 16-40 mg for detectable curative effect; while the medication is administered 3-5 times each weeks for malignant tumors, with a dose of 16-80 mg for detectable curative effect.

Compared with the known art, the technical solution of embodiments of the present invention has following advantageous effects:

At present, the lidocaine in the "three-combined medication" combined of pingyangmycin dexamethasone and lidocaine acts as a local narcotic drug, and its combination with pingyangmycin only relieves the local pain stimulation after the injection of pingyangmycin, and is not helpful for the treatment of vascular malformation and tumors, it brings no synergistic effect but an increased risk of anaphylactic shock. Compared with the prior art, the pharmaceutical composition (can be called "new three-combined medication") of embodiments of the present invention contains a certain amount of epinephrine instead of lidocaine to contract blood vessels spreading over the injection area and slow down the progress of bleomycinantitumor antibiotic (such as pingyangmycin) entering the blood circulation all over the body, which is not only helpful to maintain the pharmaceutical effect concentration in pathological tissue but also decreases the bleeding; in addition, the synergy of epinephrine and dexamethasone can prevent and alleviate the potential serious adverse reactions, such as anaphylactic shock, dyspnea and hyperpyrexia, etc., caused by pingyangmycin.

The pharmaceutical composition of embodiments of the present invention can be prepared in a form of protein microspheres to further slow down the progress of bleomycin antitumor antibiotic (such as pingyangmycin) entering the blood circulation; the pharmaceutical composition of embodiments of the present invention can also be prepared in a dosage form of magnetic nano-microspheres, control-released magnetic nano-microspheres, or targeting magnetic nano-microspheres by adhering to the magnetic nano particles,. After being injected to a patient, the magnetic nano-microspheres can stay at the focal area under the external magnetic force (for example, a magnetic device at the external of organism is provided to exert a magnetic force to secure the magnetic compound pharmaceutical microsphere at the focal area), and the targeting magnetic nano-microspheres can exert better lethal effects by specific binding between binding proteins, agglutinins or humanized antibodies and targeting cells. The pharmaceutical composition of embodiments of the present invention in a dosage form of magnetic nano-microspheres is particularly suitable for arteriovenous blood vessel malformations with rich blood.

The pharmaceutical composition of embodiments of the present invention may be applied in the treatment of vascular diseases and tumors through tumor-intracavitary injection, and patients reflected that slight but tolerable pains were caused in the injection area without local anaesthesia.

After injection, patients didn't take any analgesics, and the swelling in diseased area appeared slowly and was reduced gradually after two weeks. The pharmaceutical composition of embodiments of the present invention won't bring numbness caused by narcotic injection and risk of anaphylactic shock, because of the absence of lidocaine. Besides, the epinephrine in the pharmaceutical composition of embodiments of the present invention can effectively contract blood vessels and decrease the blood flow speed, thereby postponing the progress of drug in the diseased area entering the blood circulation and enabling the drug to stay in the intracavity longer, so as to improve therapeutic effects. In addition, the pharmaceutical composition of embodiments of the present invention can reduce the risk of anaphylactic shock effectively.

BRIEF DESCRIPTION

Some of the embodiments will be described in detail, with reference to the following figures, wherein like designations denote like members, wherein:

FIG. 1 shows a bottle filled with prepared compound pingyangmycin injection product of embodiments of the present invention;

FIGS. 2A and 2B shows the effect before/after the injection of the product of embodiments of the present invention applied to treat lingual venous malformation;

FIGS. 3A and 3B shows the effect before/after the injection of the product of embodiments of the present invention applied to treat lower-lip venous malformation;

FIGS. 4A-4D, wherein FIGS. 4A and 4C are the frontal view and lateral view of the right cheek of a patient suffered from mixed venous-lymphatic malformation respectively; FIGS. 4B and 4D are the frontal view and lateral view of the right cheek of a patient, after the treatment with the product of embodiments of the present invention.

DETAILED DESCRIPTION

Embodiments of the present invention will be further explained with reference to embodiments.

EXAMPLE 1

Preparation of Compound Pingyangmycin Injection

The preparation is conducted as following process.

Weight pingyangmycin, dexamethasone and epinephrine, dissolve the pingyangmycin and dexamethasone in water and dissolve the epinephrine in hydrochloric acid, and subsequently mix them to obtain a mixed aqueous solution; adjust the pH to 4.0-6.5 with hydrochloric acid and sodium hydroxide to obtain a compound pingyangmycin injection. The compound pingyangmycin injection comprises pingyangmycin, dexamethasone and epinephrine in a weight ratio of 2:1:0.0001, and the total weight of these three ingredients accounts for 0.3 wt. % of the weight of the obtained injection. The prepared compound pingyangmycin injection can be used for the direct injection of focal tumor cavity directly, or can be injected after being diluted to the required concentration with normal saline or glucose injection as medically indicated.

EXAMPLE 2

Preparation of Compound Pingyangmycin Injection

The pingyangmycin freeze-dried powder-injection (purchased from Tianjin Taihe Pharmaceutical Co., Ltd) is used as bottle A, and is reserved for later use; mix the epinephrine injection (purchased from Beijing YOKON Pharmaceutical Co., Ltd) and the dexamethasone injection (purchased from Henan Runhong Pharmaceutical Co., Ltd) in a proper proportion to obtain a bottle B, which is called as epinephrine and dexamethasone injection, reserve it for later use; mix the pingyangmycin freeze-dried powder-injection and dexamethasone injection containing epinephrine to obtain a compound pingyangmycin injection. The compound pingyangmycin injection comprises pingyangmycin, dexamethasone and epinephrine in a weight ratio of 2:1.25:0.0001, and the total weight of these three ingredients accounts for 0.298 wt. % of the weight of the obtained compound pingyangmycin injection. FIG. 1 shows the appearance figure of a bottle filled with prepared injection. The prepared compound pingyangmycin injection can be used for the direct injection of focal tumor cavity directly, or can be injected after being diluted to the required concentration with normal saline or glucose injection as medically indicated. The preparation method in example 2 could substitute that in example 1.

EXAMPLE 3

Preparation of Compound Pingyangmycin Freeze-Dried Powder-Injection

The preparation is conducted as follows.

Weight pingyangmycin, dexamethasone and epinephrine, dissolve the lidocaine pingyangmycin and dexamethasone in water and dissolve the epinephrine in hydrochloric acid, and subsequently mix them to obtain a mixed aqueous solution; adjust the pH to 4.0-6.5 with hydrochloric acid and sodium hydroxide, and perform freeze-drying after dispensing to obtain a compound pingyangmycin freeze-dried powder-injection. The compound pingyangmycin freeze-dried powder-injection comprises pingyangmycin, dexamethasone and epinephrine in a weight ratio of 8:5:0.0001, and the total weight of these three ingredients accounts for 85 wt. % of the weight of the compound pingyangmycin freeze-dried powder-injection. The freeze-dried powder-injection is dispensed into bottles, and 8 mg pingyangmycin, 5 mg dexamethasone and 0.0001 mg epinephrine are contained in each bottle. When used, the compound pingyangmycin freeze-dried powder-injection is dissolved with normal saline or glucose injection, to obtain a compound pingyangmycin injection.

EXAMPLE 4

Preparation of Compound Pingyangmycinalbumin Microspheres

The preparation is conducted as following process.

1) Weight pingyangmycin, dexamethasone and epinephrine, then dissolve the lidocaine pingyangmycin and dexamethasone in water and dissolve the epinephrine in hydrochloric acid, and subsequently mix them to obtain a compound pingyangmycin solution.

2) Prepare compound pingyangmycin albumin microspheres through emulsifying-curing method: well mixing the obtained compound pingyangmycin solution of step 1) with 20 wt. % human albumin solution, cure the mixture with glutaraldehyde after ultrasonic homogenization, and then wash repeatedly, finally dry and collect it to obtain compound pingyangmycin albumin microspheres. The compound pingyangmycin albumin microspheres comprise pingyangmycin, dexamethasone and epinephrine in a weight ratio of 8:5:0.0001, and the total weight of these three ingredients accounts for 60% of the weight of the compound pingyangmycin albumin microspheres. The compound pingyangmycin albumin microspheres are dispensed into bottles, and 8 mg pingyangmycin, 5 mg dexamethasone and 0.0001 mg epinephrine are contained in each bottle.

EXAMPLE 5

Preparation of Compound Pingyangmycin Magnetic Nano-Microspheres

The preparation is conducted as following process.

Dissolve the sodium alginate sealing agent and silica-wrapped magnetic nano-microspheres in an aqueous solution in a proper proportion, stir and add the compound pingyangmycin solution prepared as the process of step 1) in example 4. Then add liquid paraffin containing Span85 slowly, place it in an ice bath after emulsifying, add formaldehyde and isopropanol successively, and filtrate after stirring, then wash them with anhydrous ether and acetone, finally dry and sieve them to obtain the compound pingyangmycin magnetic nano-microspheres. The compound pingyangmycin magnetic nano-microspheres formulation comprises pingyangmycin, dexamethasone and epinephrine in a weight ratio of 8:2:0.0001, and the total weight of these three ingredients accounts for 30% of the weight of the compound pingyangmycin magnetic nano-microspheres formulation. The microspheres formulations are dispensed into bottles, and 8 mg pingyangmycin, 2 mg dexamethasone and 0.0001 mg epinephrine are contained in each bottle.

EXAMPLE 6

Preparation of Compound Pingyangmycin Control-Released Magneticnano-Microspheres Formulation The preparation is conducted as following process.

1) Prepare compound pingyangmycin solution according to the process of step 1) in example 4;

2) Add dichloromethane solution in which carbon-coated iron (Fe@C) nano-microspheres and poly lactide-glycolide acid (PLGA) have been dissolved in the pre-emulsifying reactor, then add the obtained compound pingyangmycin solution in step 1) in the pre-emulsifying reactor, stir at a high speed to obtain a water-in-oil compound pingyangmycin pre-emulsion, which is subsequently added slowly into the PVA aqueous solution and stirred to form a water-in-oil-in-water (W/O/W) multiple emulsion, then slow down the stirring rate and obtain the compound pingyangmycin PLGA microspheres after gradual curing, and dry the microspheres through freeze-drying method after washing to obtain the compound pingyangmycin control-released magnetic nano-microspheres formulation. The compound pingyangmycin control-released magnetic nano-microspheres formulation comprises pingyangmycin, dexamethasone and epinephrine in a weight ratio of 8:5:0.0001, and the total weight of these three ingredients accounts for 28% of the weight of the compound pingyangmycin control-released magnetic nano-microspheres formulation. The microspheres formulations are dispensed into bottles, and 8 mg pingyangmycin, 5 mg dexamethasone and 0.0001 mg epinephrine are contained in each bottle.

EXAMPLE 7

Preparation of Compound Pingyangmycin Targeted Magnetic Nano-Microspheres Formulation The preparation is conducted as following process.

Prepare compound pingyangmycin magnetic nano-microspheres according to the process of example 5; mix the dolichos bifows agglutinin (DBA) solution with the compound pingyangmycin magnetic nano-micropheres before drying, to make the dolichos bifows agglutinin (DBA) adhere to the surface of nano-microsphere, dry them through freeze-drying method after washing to obtain the compound pingyangmycin targeted magnetic nano-micropheres formulation. The compound pingyangmycin targeted magnetic nano-micropheres formulation comprises pingyangmycin, dexamethasone and epinephrine in a weight ratio of 8:2:0.0001, and the total weight of these three ingredients accounts for 28% of the weight of the compound pingyangmycin targeted magneticnano-microphere formulation. The microspheres formulations are dispensed into bottles, and each bottle has 8 mg pingyangmycin, 2 mg dexamethasone, 0.0001 mg epinephrine.

APPLICATION EXAMPLE

The pharmaceutical composition of embodiments of the present invention is well effective in treatment of vascular diseases and tumors, and several typical application examples are illustrated as follows.

Application Example 1

Usage of the Pharmaceutical Composition of Embodiments of the Present Invention in Treatment of Tongue-Tip Venous Malformation WANG was found venous malformation in the tongue-tip, shown as a livid swelling, before treatment. Compound pingyangmycin injection was used for treatment. Before injection, dilute the compound pingyangnycin injection with normal saline to obtain an injection containing 1 mg pingyangmycin, 0.625 mg dexamethasone and 0.00005 mg epinephrine for every 0.5 ml injection. Perform tumor-intracavity injection with 0.5 ml diluted injection, and repeat the injection after two weeks. As a result, the livid swelling in tongue-tip of the patient almost disappears, and the photographs of tongue-tip of the patient before and after the injection are shown in FIGS. 2A and 2B respectively. During the treatment, no severe adverse reaction, such as anaphylactic shock, hard breath and hyperpyrexia, etc., occurred for the patient.

The compound pingyangmycin injection used in the example can be prepared according to the process of example 2.

Application Example 2

Usage of the Pharmaceutical Composition of Embodiments of the Present Invention in Treatment of Venous Malformation in Lower Right Lip LI was found venous malformation in the lower right lip, shown as a livid swelling and hypertrophy, before treatment. Compound pingyangmycin injection was used for treatment. Before injection, dilute the compound pingyangnycin injection with normal saline to obtain an injection containing 7 mg pingyangmycin, 4.3755 mg dexamethasone and 0.00035 mg epinephrine for every 3.5 ml injection. Perform tumor-intracavity injection with 3.5 ml diluted injection, and repeat the injection after two weeks. As a result, the livid swelling in tongue-tip of the patient almost disappears, both sides of the lower lip are nearly symmetrical, and the photographs of lips of patient before and after the injection are shown in FIGS. 3A and 3B respectively. During the treatment, no severe adverse reaction, such as anaphylactic shock, hard breath and hyperpyrexia, etc., occurred for the patient.

The compound pingyangmycin injection used in the example can be prepared according to the process of example 2.

Application Example 3

Usage of the Pharmaceutical Composition of Embodiments of the Present Invention in Treatment of Mixed Vein and Lymphatic Malformation in Cheek ZHOU was found obvious hypertrophy in the right cheek and livid venous malformation on the surface of skin, before treatment. Compound pingyangmycin injection was used for treatment. Before injection, dilute the compound pingyangnycin injection to obtain an injection containing 8 mg pingyangmycin, 5 mg dexamethasone and 0.002 mg epinephrine for 4 ml injection in each bottle. Perform tumor-intracavity injection with 4 ml diluted injection, and repeat the injection after four weeks. As a result, the hypertrophy in right cheek of the patient is significantly reduced and the livid area in the skin almost disappears. Front and lateral photographs of mixed venin and lymphatic malformation in right cheek of the patient before treatment are shown in FIGS. 4A and 4C, and the front and lateral photographs of right cheek are shown in FIGS. 4B and 4D. During the treatment, no severe adverse reaction, such as anaphylactic shock, hard breath and hyperpyrexia, etc., occurred for the patient.

The compound pingyangmycin injection used in the example can be prepared according to the process of example 1.

Application Example 4

Usage of the Pharmaceutical Composition of Embodiments of the Present Invention in Treatment of Maxillary Gingiva Squamous-Cell Carcinoma ZHU was found swelling in maxillary gingiva before treatment. Compound pingyangmycin injection was used for treatment. Before injection, dilute the compound pingyangnycin injection with normal saline to obtain an injection containing 8 mg pingyangmycin, 10 mg dexamethasone and 0.0001 mg epinephrine for every 8 ml injection. During treatment, perform tumor-intracavity injection with 8 ml diluted injection. After treatment, the swelling in maxillary gingiva of the patient is relived. During the treatment, no severe adverse reaction, such as anaphylactic shock, hard breath and hyperpyrexia, etc., occurred for the patient.

The compound pingyangmycin injection used in the example can be prepared according to the process of example 1.

The compound pingyangmycin injection used in above application examples may also be compound formulations in other dosage forms, such as compound pingyangmycin injection freeze-dried powder-injection, or microspheres, and the dilution and dissolution should be conducted before usage.

Substances in above examples were purchased from the market, if no special explanation was made. Those contents not been specially explained in the preparation method are technologies known for one skilled in the art or can be obtained from prior art.

Although the present invention has been disclosed in the form of preferred embodiments and variations thereon, it will be understood that numerous additional modifications and variations could be made thereto without departing from the scope of the invention.

For the sake of clarity, it is to be understood that the use of 'a' or 'an' throughout this application does not exclude a plurality, and 'comprising' does not exclude other steps or elements.

The invention claimed is:

1. An anti-vascular malformation pharmaceutical composition, wherein the pharmaceutical composition comprises effective ingredients comprising pingyangmycin, dexamethasone and epinephrine or pharmaceutically acceptable salts thereof in a weight ratio of 7:4.3755:0.00035.

2. The pharmaceutical composition according to claim 1, wherein a total weight of the pingyangmycin, dexamethasone, and epinephrine accounts for 20%-90% of the weight of the pharmaceutical composition.

3. The pharmaceutical composition according to claim 1, wherein the pharmaceutical composition further comprises a pharmaceutically acceptable auxiliary.

4. The pharmaceutical composition according to claim 3, wherein the pharmaceutically acceptable auxiliary comprises at least one of a pH regulator and mannitol.

5. The pharmaceutical composition according to claim 1, wherein the pharmaceutical composition is in a dosage form of injection, freeze-dried powder, or microspheres.

6. The pharmaceutical composition according to claim 5, wherein the microspheres are albumin microspheres, magnetic nano-microspheres, control-released magnetic nano-microspheres, or cellular targeted magnetic nano-microspheres.

7. A method for treating vascular malformations, comprising the step of:
   preparing a medication comprising the pharmaceutical composition of claim 1;
   administering the medication to a patient suffering from the vascular malformations.

8. The method for treating vascular malformations, comprising the step of:
   preparing a medicine comprising the pharmaceutical composition of claim 2;
   administering the medication to a patient suffering from the vascular malformations.

9. The method for treating vascular malformations, comprising the step of:
   preparing a medicine comprising the pharmaceutical composition of claim 3;
   administering the medication to a patient suffering from the vascular malformations.

10. The method for treating vascular malformations, comprising the step of:
    preparing a medicine comprising the pharmaceutical composition of claim 4;
    administering the medication to a patient suffering from the vascular malformations.

11. The method for treating vascular malformations, comprising the step of:

preparing a medicine comprising the pharmaceutical composition of claim 5;
   administering the medication to a patient suffering from the vascular malformations.

12. The method for treating vascular malformations, comprising the step of:
preparing a medicine comprising the pharmaceutical composition of claim 6;
   administering the medication to a patient suffering from the vascular malformations.

* * * * *